(12) United States Patent
Gabbiani et al.

(10) Patent No.: US 6,335,320 B1
(45) Date of Patent: Jan. 1, 2002

(54) METHOD OF TREATING FIBROTIC CONDITIONS

(75) Inventors: Giulio Gabbiani, Geneva (CH); Alain Scarso, Courcelles (BE)

(73) Assignee: UCB S.A., Brussels (BE)

( * ) Notice: Subject to any disclaimer, the term of this patent is extended or adjusted under 35 U.S.C. 154(b) by 0 days.

(21) Appl. No.: 09/466,772

(22) Filed: Dec. 20, 1999

(30) Foreign Application Priority Data

Dec. 24, 1998 (EP) .............................................. 98204396

(51) Int. Cl.[7] .............................................. C07K 14/00
(52) U.S. Cl. ........................... 514/14; 514/18; 530/326; 530/327; 530/328; 530/330
(58) Field of Search ...................... 514/14, 18; 530/326, 530/327, 328, 330

(56) References Cited

U.S. PATENT DOCUMENTS

| | | | |
|---|---|---|---|
| 5,254,342 A | 10/1993 | Shen et al. | 424/407 |
| 5,534,496 A | 7/1996 | Lee et al. | 514/17 |
| 5,783,662 A | 7/1998 | Janmey et al. | 530/328 |
| 5,837,533 A | 11/1998 | Boutin | 435/320.1 |
| 5,846,743 A | 12/1998 | Janmey et al. | 435/7.8 |

FOREIGN PATENT DOCUMENTS

| | | |
|---|---|---|
| EP | 0 497 997 A1 | 8/1993 |
| WO | WO 99/11809 | 3/1999 |
| WO | WO 00/01417 | 1/2000 |

*Primary Examiner*—Karen Cochrane Carlson
(74) *Attorney, Agent, or Firm*—Wenderoth, Lind & Ponack, L.L.P.

(57) ABSTRACT

The present invention is related to a peptidic product comprising the tetrapeptide Acetyl-glutamyl-glutamyl-glutamyl-aspartyl (SEQ ID No:5) associated with a chemical entity that is able to introduce said tetrapeptide into a cell. The present invention is also related to the pharmaceutical composition comprising at least one pharmaceutically acceptable excipient and an effective amount of the peptidic product according to the invention.

13 Claims, No Drawings

METHOD OF TREATING FIBROTIC CONDITIONS

BACKGROUND OF THE INVENTION

1. Field of the Invention

PEPTIDIC PRODUCT, PROCESS and COMPOSITION

The present invention relates to a peptidic product comprising an active tetrapeptide Acetyl-glutamyl-glutamyl-glutamyl-aspartyl (SEQ ID No. 5) associated with a vector which allows the introduction of said tetrapeptide into a cell.

The present invention is also related to pharmaceutical compositions comprising said peptidic product and to its use for the prevention and/or the treatment of wound contractions, hypertrophic scars, fibromatosis, in particular the so-called Dupuytren disease and fibrotic conditions (in particular lung fibrosis).

2. Description of the Related Art

Skalli et al. (J. of Cell Biology Vol. 103 No. 6, pp. 2787–2796 (1986)) describe that an antibody (anti-alpha SM-1) recognising exclusively the alpha smooth muscle (α-SM) actin could be selected and characterised after immunisation of BALB/c mice with the amino terminal synthetic decapeptide of α-SM actin coupled to a carrier molecule.

It is also known that the α-SM actin is transiently expressed in myofibroblast during experimental wound healing (Darby et al., Laboratory Investigation Vol. 63, 21–29 (1990)). Chaponnier et al. (J. of Cell Biology Vol. 130 No. 4, 887–895 (1995)) describes the blocking effects of an amino terminal decapeptide of a-SM actin (AcEEEDSTALVC) (SEQ ID No: 6) on the binding of specific monoclonal antibody anti-alpha SM-1. This document indicates that the portion AcEEED (SEQ ID No: 5) is the epitope for the anti-alpha SM-1.

The anti-alpha SM-1 is the first monoclonal antibody described to be specific for a single actin isoform and is a reliable tool for the study of vascular SM cells and myofibroblast phenotypic modulation in physiological and pathological processes.

This document shows that said antibody (especially its Fab fragment) increases in vitro α-SM actin polymerisation. Said document also suggests that the tetrapeptide AcEEED (SEQ ID No: 5) may be used for the study of the functions of the α-SM actin in cells such as SM cells, fibroblasts, myofibroblasts or myoepithelial cells in physiological and pathological situation during which α-SM actin expression is modulated. Said document also suggests that the tetrapeptide AcEEED (SEQ ID No: 6) inhibits the incorporation of α-SM actin into stress fibers in the culture of SM cells when using microinjection technology.

It is also shown that an active turnover of α-SM actin into stress fibers exists and that AcEEED (SEQ ID No: 5) traps a protein interacting with the amino-terminal sequence of α-SM actin and activating polymerization (Chaponnier, C. et al., Experientia, 1995, 51, A62).

Järlebark, L. et al. (Biochemical and Biophysical Research Communications, 1996, 229 (2), 363–369), disclose that some peptidyl derivatives of adenosine 5'-carboxylic acid have inhibitory effects in certain P2 purinoceptor-carrying biological systems (gliome and smooth muscle cell lines and isolated smooth muscle tissue preparations).

The present invention aims to provide a peptidic product comprising the specific tetrapeptide AcEEED (SEQ ID No: 5) which allows its introduction into a cell, in order to interfere, in vitro and in vivo, with α-SM-actin organisation in stress fibers.

Another aim of the present invention is to provide a pharmaceutical composition comprising said peptidic product in order to treat and/or to prevent various diseases related to α-SM actin expression such as wound contraction, hypertrophic scars, fibromatosis, in particular Dupuytren diseases, and fibrotic condition (in particular lung fibrosis).

SUMMARY OF THE INVENTION

The present invention is related to a peptidic product comprising the active tetrapeptide Acetyl-glutamyl-glutamyl-glutamyl-aspartyl (SEQ ID No: 5) (identified hereafter by the formulation AcEEED) associated with a chemical entity which is able to introduce said tetrapeptide into a cell.

DESCRIPTION OF THE PREFERRED EMBODIMENTS

According to the invention, in the active tetrapeptide Ac means Acetyl, E means glutamic acid residue, D means aspartic acid residue.

According to the invention, by a chemical entity we understand a vector.

According to the invention, by a cell we understand in vivo cells, such as cells composing the organs or tissues of living animals or humans, or microorganisms found in living animals or humans; or in vitro cells,such as cultured animal cells, human cells or microorganisms. Preferably it means human cells, and more preferably fibroblastic or smooth muscle cells.

According to a first embodiment of the present invention, the chemical entity can be a liposome, a lipidic vesicle made of lipids and/or fatty acids or a cationic vesicle such as the one described by Gao X. and Huang L. (Cationic Liposomes - Mediated Gene Transfer, Gene Therapy, pp. 710–722 (1995)) and/or a mixture thereof.

According to a second embodiment of the present invention, the chemical entity is a polypeptide having preferably at least about 8 amino acids, preferably between 8 and 40, more preferably between 10 and 30 amino acids.

According to another embodiment of the present invention, said polypeptide is the tat mediated protein, having advantageously a capacity of binding with membranous receptor(s) of specific cell(s).

The preferred linking of a chemical entity like the tat mediated protein to the tetrapeptide according to the invention for the delivery of heterologous peptides into a cell, is described in the International Patent Publication WO 94/04686 incorporated herein by reference. The best results have been obtained with the tat mediated protein of formula tat37-72, tat37-58, tat38-58GGC, tatCGG47–58, tat47-58GGC and tatΔC.

According to a preferred embodiment of the present invention, the chemical entity is a homeobox peptide, preferably the pAntp peptide described in the International Patent Publication WO 97/12912, also incorporated herein by reference. The best results have been obtained with the peptide pAntp[43–58], and the peptide pAntp[43–58]-Pro$^{50}$. The peptide pAntp[43–58] means Arg-Gln-Ile-Lys-Ile-Trp-Phe-Gln-Asn-Arg-Arg-Met-Lys-Trp-Lys-Lys, (SEQ ID No: 7) wherein, for this description, the first amino acid Arg is named amino acid in position 43 and the last amino acid Lys is named amino acid in position 58. The peptide pAntp[43–58]-Pro$^{50}$ (SEQ ID No: 7) represents the same sequence of pAntp[43–58]wherein Gln has been substituted by Pro in position 50.

The present invention relates also to the preparation method of such product, using known methods by the person skilled in the art such as preparation methods of lipidic vesicles (Martin F. G., *Pharmaceutical Manufacturing of Liposomes*, Praveen Tyle Ed., Specialised Drug Delivery Systems, Marcel Decker, N.Y. (1993)), automatic peptides synthesis, cross-linking between olecules.

Possibly, the tetrapeptide is linked through a spacer, preferably a peptidic spacer, to the chemical entity. Said spacer is preferably an amino acid or a peptide comprising no more than 5 amino acids. Preferably, said amino acid used as a spacer is a Lysyl residue ("K") to which the AcEEED (SEQ ID No: 7) tetrapeptide is linked through the α-amino group, or through the ε-amino group, or a Cystinyl residue (meaning two Cysteinyl residues ("C") linked by their β sulfide functions forming a disulfide link represented by "C-[S-S]-C") to which the AcEEED (SEQ ID No: 5) tetrapeptide is linked through the α-amino group, or β-Alanyl-β-Alanyl dipeptide ("β-A-β-A") to which the AcEEED (SEQ ID No: 5) tetrapeptide is linked through the ε-amino group, or through a Lysyl residue ("K") to which the AcEEED (SEQ ID No: 5) tetrapeptide is linked through the ε-amino group and a BiotynylGG residue (meaning a biotinyl functionnal group linked through its carboxylic function to two successive glycyl residues) to which the AcEEED (SEQ ID No: 5) tetrapeptide is linked through the α-amino group.

The best results have been obtained with the AcEEED (SEQ ID No: 5) tetrapeptide linked through the α-amino group, or through the ε-amino group of a Lysyl residue.

According to the invention, the peptidic product is preferably selected from the group consisting of ε-(AcEEED)-K-(pAntp[43–58]), (SEQ ID No: 1)
AcEEED-β-A-β-A-(pAntp[43–58]), (SEQ ID No: 2)
AcEEED-K-(pAntp[43–58]), (SEQ ID No: 2)
AcEEED-β-A-β-A-(pAntp[43–58]Pro$^{50}$), (SEQ ID No: 2)
AcEEED-K-(pAntp[43–58]-Pro$^{50}$), (SEQ ID No: 1)
AcEEED- (pAntp[43–58]-Pro$^{50}$), (SEQ ID No: 3)
AcEEED-(pAntp[43–58]), (SEQ ID No: 3)
AcEEED-C-[S-S]-C-(pAntp[43–58]), (SEQ ID No: 2)
AcEEED-C- [S-S]-C- (pAntp[43–58]-Pro$^{50}$) (SEQ ID No: 2)
α-(BiotynylGG),ε-(AcEEED)-K-(pAntp[43–58]), (SEQ ID No: 4)
ε-(AcEEED)-K-(pAntp[43–58]-Pro$^{50}$), (SEQ ID No: 1)
α-(BiotynylGG),ε-(AcEEED)-K-(pAntp[43–58]-Pro$^{50}$), (SEQ ID No: 4)

The peptidic product is more preferably selected from the group consisting of

AcEEED-K-(pAntp[43–58]), represented by the following structure: ε-(AcEEED)-K-RQIKIWFQNRRMKWKK-OH (SEQ ID No: 1) (identified hereafter by the term "product 1");

AcEEED-K-(pAntp[43–58]), represented by the following structure: AcEEED-K-RQIKIWFQNRRMKWKK-OH (SEQ ID No: 1) (identified hereafter by the term "product 2");

AcEEED-β-A-β-A-(pAntp[43–58]), represented by the following structure: AcEEED-β-A-β-A-RQIKIWFQNRRMKWKK-OH (SEQ ID No. 2) (identified hereafter by the term "product 3");

AcEEED-(pAntp[43–58]), represented by the following structure: AcEEED-RQIKIWFQNRRMKWKK-OH (SEQ ID No: 3) (identified hereafter by the term "product 4");

AcEEED-C-[S-S]-C-(pAntp[43–58]), represented by the following structure: AcEEED-C-[S-S]-C-RQIKIWFQNRRMKWKK- OH (SEQ ID No: 2) (identified hereafter by the term "product 5");

α-(BiotynylGG),ε-(AcEEED)-K-(pAntp[43–58]), represented by the following structure: α-(Biotinyl-GG), ε-(AcEEED)-K-RQIKIWFQNRRMKWKK-OH (SEQ ID No: 4) (identified hereafter by the term "product 6");

ε-(AcEEED)-K-(pAntp[43–58]-Pro$^{50}$), represented by the following structure: ε-(AcEEED)-K-RQIKIWFPNRRMKWKK-OH (SEQ ID No: 1) (identified hereafter by the term "product 7");

α-(BiotynylGG),ε-(AcEEED)-K-(pAntp[43–58]-Pro$^{50}$), represented by the following structure: α-(BiotinylGG), ε-(AcEEED)-K-RQIKIWFPNRRMKWKK-OH (SEQ ID No: 4) (identified hereafter by the term "product 8").

The best results have been obtained with the product α-(BiotynylGG),ε-(AcEEED)-K-(pAntp[43–58]-Pro $^{50}$) (SEQ ID No: 4) and the product ε-(AcEEED)-K-(pAntp[43–58]).

In products 1 to 8, α-( )-K- means that functionnal group in brackets is linked on the alpha-amino group of lysyl residue; ε-( )-K- means that functionnal group in brackets is linked on the epsilon-amino group of lysyl residue; -β-A represents beta-alanyl residue; and -C-[S-S]-C represents two cysteinyl residues linked through their β sulfide function, forming a disulfide bridge. Products 1, 5 to 8 are not linear, are branched sequences; products 2, 3 and 4 are linear, are unbranched sequences. In the sequence listing, product 2 is represented by the sequence SEQ ID NO:1; product 3 is represented by the sequence SEQ ID NO:2, where Xaa means β Ala; and product 4 is represented by the sequence SEQ ID NO:3.

Product 1 is ε-(Acetyl Glu Glu Glu Asp) Lys Arg Gln Ile Lys Ile Trp Phe Gln Asn Arg Arg Met Lys Trp Lys Lys OH (SEQ ID No: 1).

Product 2 is Acetyl Glu Glu Glu Asp Lys Arg Gln Ile Lys Ile Trp Phe Gln Asn Arg Arg Met Lys Trp Lys Lys OH (SEQ ID No: 1).

Product 3 is Acetyl Glu Glu Glu Asp βAla βAla Arg Gln Ile Lys Ile Trp Phe Gln Asn Arg Arg Met Lys Trp Lys Lys OH (SEQ ID No: 2).

Product 4 is Acetyl Glu Glu Glu Asp Arg Gln Ile Lys Ile Trp Phe Gln Asn Arg Arg Met Lys Trp Lys Lys OH (SEQ ID No: 3).

Product 5 is Acetyl Glu Glu Glu Asp Cys[S-S]Cys Arg Gln Ile Lys Ile Trp Phe Gln Asn Arg Arg Met Lys Trp Lys Lys OH (SEQ ID No: 2).

Product 6 is α-(Biotinyl Gly Gly) ε-(Acetyl Glu Glu Glu Asp) Lys Arg Gln Ile Lys Ile Trp Phe Gln Asn Arg Arg Met Lys Trp Lys Lys OH (SEQ ID No: 4).

Product 7 is ε-(Acetyl Glu Glu Glu Asp) Lys Arg Gln Ile Lys Ile Trp Phe Pro Asn Arg Arg Met Lys Trp Lys Lys OH (SEQ ID No: 1).

Product 8 is α-(Biotinyl Gly Gly) ε-(Acetyl Glu Glu Glu Asp) Lys Arg Gln Ile Lys Ile Trp Phe Pro Asn Arg Arg Met Lys Trp Lys Lys OH (SEQ ID No: 4).

The present invention concerns also a process for preparing the peptidic product comprising the active tetrapeptide AcEEED (SEQ ID No: 5) associated with a chemical entity.

The peptidic product of the invention can be prepared using known methods by the person skilled in the art, such as the step-wise solid-phase synthesis, the straightforward synthesis of a peptide, the synthetic or biologic preparation of peptide (described for examples in "The peptides, Analysis, Synthesis, Biology"; vol. 1 to 9, S. Udenfriend, J.

Meienhofer, eds, 1977 to 1987, Academic Press, New-York; or in "Methods in Molecular Biology", vol. 35, Peptide Synthesis Protocols, M. W. Pennington & B. M. Dunn (Eds), 1994, Humana Press, Totowa N.J.).

The present invention concerns also a peptidic product comprising the active tetrapeptide AcEEED (SEQ ID No: 5) associated with a chemical entity for use as a medicament.

Another aspect of the present invention concerns a pharmaceutical composition comprising at least one pharmaceutically acceptable carrier, vehicle or excipient and the peptidic product.

A medical preparation with the said pharmaceutical composition has been applied topically at an effective dose of 1–3 mg peptide/1 ml saline, resulting in the best efficacy according to the present invention.

For implementing the method of treatment of the invention, the pharmaceutical composition herein above described should contain an effective amount of the peptidic product. An effective amount can be readily determined by the use of conventional techniques and by observing results obtained under analogous circumstance. In determining the effective amount, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective amount of the peptidic product in the composition of the invention will generally vary from about 1 microgram per kilogram of body weight per day ($\mu$g/kg/day) to about 500 milligram /kg body weight/day. A posology (dose) of about 100 $\mu$g to about 10 mg once or twice per day is preferred.

The medical preparation with the said pharmaceutical composition can be formulated in any form and administered by various routes or modes, including but not limited to intravenous injection, intramuscular injection, inhalation, transmucosal or transdermal delivery, nasal administration, oral administration, intestinal and rectal administration, according to clinical indications. A person skilled in the art of preparing formulations can readily select the proper form and mode of administration depending upon the particular characteristics of the disease state to be treated, the stage of the disease, and other relevant circumstances.

The compositions of the invention can comprise the peptidic product in combination with at least one pharmaceutically acceptable carrier or excipient, the proportion and nature of which are determined by the solubility and chemical properties of the composition selected, the chosen route of administration, and standard pharmaceutical practice.

More particularly, the present invention contemplates pharmaceutical compositions consisting essentially of a therapeutically effective amount of the above-described peptidic product in admixture or otherwise in association with one or more pharmaceutically acceptable carriers or excipients (collectively referred to hereafter as "carrier" materials).

The carrier material may be a solid, semi-solid, or liquid material which can serve as a vehicle or medium for the active ingredient. Suitable carrier materials are well known in the art. The pharmaceutical compositions of the invention may be adapted for topical, injection or other use and may be administered to the patient in the form of injection, cream, ointment, powders, elixirs, syrups, solutions, suspensions, or the like. The pharmaceutical composition of the invention may also be adapted for rectal use and may then be administered to the patient in the form of suppositories.

The carrier material should be suitably selected with respect to the intended form of administration, and consistent with conventional pharmaceutical practice. Optionally, the pharmaceutical composition of the invention also contain a binder such as microcrystalline cellulose, gum or gelatine, a disintegrating agent such as alginic acid, a lubricant such as magnesium stearate, a glidant such as colloidal silicon dioxide, a sweetening agent such as sucrose or saccharin, a coloring agent or a flavouring agent such as peppermint or methyl salicylate.

Because of their easy administration, cream and solution represent the most advantageous topical dosage unit form.

In addition to the common dosage forms set out above, the compositions of the present invention may also be administered by controlled release means and delivery devices.

Such solutions or cream may also include one or more of the following adjuvants: a sterile diluent such as water for injection, physiologic saline solution, oils, polyethylene glycols, glycerine, propylene glycol or other synthetic solvents; antibacterial agents such as benzyl alcohol; antioxidants such as ascorbic acid or sodium bisulfite; chelating agents such as ethylene diaminetetraacetic acid; buffers such as acetates, citrates or phosphates and agents for adjusting of tonicity such as sodium chloride or dextrose. The preparation can be enclosed in ampules, or multiple dose vials made of glass or plastic.

The pharmaceutically acceptable excipient may vary according to the mode of administration and could be combined with an adjuvant in order to improve the therapeutical properties of the pharmaceutical composition or reduce its possible side-effects.

Suitable pharmaceutically acceptable excipients are well known in the art and are selected according to the methods generally applied by pharmacists or doctors, and may include solid, liquid or gaseous, non-toxic pharmaceutically acceptable vehicles. The percentage of active product versus pharmaceutically acceptable excipient may vary within very large ranges, only limited by the tolerance and the possible side-effects upon the animal, including the human, and by the frequency of administration.

The present invention concerns also the use of said pharmaceutical composition or said peptidic product for the manufacture of a medicament. The present invention concerns also the use of said pharmaceutical composition or said peptidic product for the manufacture of a medicament in the prevention and/or the treatment of a disease related to $\alpha$-SM actin expression into a cell (surexpression into a cell or expression in a cell which normally does not express $\alpha$-SM actin). Preferably, said disease is selected from the group consisting of wound contraction, hypertrophic scars, fibromatosis (especially Dupuytren's disease) and fibrotic conditions (especially lung fibrosis).

The invention concerns also a method for manufacturing a medicament, wherein the peptidic product is used.

Another aspect of the present invention is related to a method of treatment and/or prevention of said diseases wherein said peptidic product or said pharmaceutical composition is administered to a mammal, in particular to a human, suffering from said diseases or presenting the symptoms of said diseases.

The present invention will be described in detail in the following examples. However, these examples are merely illustrative and should not be construed to limit the spirit and scope of the claims.

EXAMPLES 1 to 8

Peptidic Products Synthesis

Peptidic products were prepared synthetically by Merrifield synthesis, as described in "The peptides, Analysis, Synthesis, Biology"; vol. 1 to 9, S. Udenfriend, J. Meienhofer, eds, 1977 to 1987, Academic Press, New-York.

The amino acids are added step by step to an insoluble resin.

Each amino acid (except Lysine) may be protected with a t-Butoxycarbonyl group (which is called Boc-) at its α-amino group and the other functionalities are protected by protecting groups:

- the hydroxyl function of Serine (S) and Threonine (T) may be protected by a benzyl group
- the guanidino function of Arginine (R) may be protected by a Tosyl group
- the amino group of the indole cycle of Tryptophane (W) may be protected by a formyl group;
- the α-amino function of Lysine (K) may be protected by a Boc- group or a fluorenylmethoxycarbonyl group (Fmoc-) or a benzyloxycarbonyl group (Z-) and the ε-amino function of Lysine may be protected by a Boc- group or a 2-chlorobenzyloxycarbonyl group
- the β-carboxylic function of aspartic acid (D) is protected by a cyclohexyl group
- the γ-carboxylic function of glutamic acid (E) is protected by a benzyl group.

The carboxylic C-terminal peptides were synthesised on a chloromethylstyrene/1% divinylbenzene resin. The amide C-terminal peptides were synthesised on a 4-methybenzhydrylamine polystyrene/1% divinylbenzene resin according to a method also described in "The peptides, Analysis, Synthesis, Biology"; vol. 1 to 9, S. Udenfriend, J. Meienhofer, eds, 1977 to 1987, Academic Press, New-York.

In the case of chloromethylstryene resin, the first amino acid (AA) is introduced as follows: the Cesium salt of the Boc-AA (Boc-AA means amino acid protected by a t-butoxycarbonyl group on its α-amino group) is formed, adding 1 equivalent of Cesium carbonate in dimethylformamide (DMF) and this salt is added to the chloromethyl resin in DMF. The mixture is stirred at 50° C. overnight.

The substitution level of the resin by the first AA is determined by amino acid analysis after hydrochloric acid (HCl) hydrolysis.

The next amino acids are added step by step using the standard procedure (method described in "The peptides, Analysis, Synthesis, Biology"; vol. 1 to 9, S. Udenfriend, J. Meienhofer, eds, 1977 to 1987, Academic Press, New-York):

- deprotection of the N-terminal Boc group of the AA on resin in trifluoroacetic acid (TFA)/$CH_2Cl_2$;
- washing with $CH_2Cl_2$;
- neutralisation in triethylamine (TEA)/$CH_2Cl_2$;
- washing with $CH_2Cl_2$;
- coupling of the next Boc-AA in the following conditions: 2.5 equivalents of the Boc-AA is preactivated in DMF with dicyclohexylcarbodiimide (DCC)/Hydroxybenzotriazole (HOBt). The activated Boc-AA-benzotriazolate obtained is added to the resin-peptide in DMF. The completion of the reaction is controlled by the Kaiser and the Chloranyl tests (as described in E. Kaiser, R. L. Colescott, L. D. Bassinger, P. I. Cook; Anal. Biochem., 34, 595 (1970) and in T. Vojkovsky, Peptide Research, vol.8, No. 4, 236–237 (1995), respectively).

If the reaction is incomplete, a recoupling procedure is used after washing of the resin-peptide with DMF: 1.25 equivalent of the Boc-AA is added together with 1.25 equivalent of 2-(1H-benzotriazole-1-yl)-1,1,3,3-tetramethyluronium tetrafluoroborate (TBTU) and 1.25 equivalent of HOBt in DMF. If one of the tests remains positive after the recoupling procedure, an acetylation of the remaining amino functions is performed using acetic anhydride;

washing with DMF, $CH_2Cl_2$, $CH_3OH$.

When all the amino acids are added, the peptide-resin is dried under vacuum and the peptide is cleaved from the resin following a standard low-high HF cleavage. The deprotected peptides so obtained are purified on reverse phase HPLC in a TFA 0.1%/$CH_3CN$ system. After lyophilisation, the pure peptide is obtained as a white powder.

The peptidic products that were tested are identified hereafter along with their characteristics.

The peptidic product of example 1 is represented by the following structure: ε-(ACEEED)-K-RQIKIWFQNRRMKWKK-OH (SEQ ID No:1. Its formula is C131 H208 N40 O34 S1. Its molecular weight(M.W.) is 2919.4. Its FAB/MS analysis gives the following results $[M+H]^+=2921$, FAB/MS means Fast Atom Bombardment Mass Spectroscopy, this analytical method is described in "Methods in Molecular Biology", vol. 36;

Peptide Analysis Protocols, M. W. Pennington & B. M. Dunn (Eds), 1994, Humana Press, Totowa N.J.

The peptidic product of example 2 is represented by the following structure: AcEEED-K-RQIKIWFQNRRMKWKK-OH (SEQ ID No:1. Its formula is C131 H208 N40 O34 S1. Its molecular weight(M.W.) is 2919.4. Its FAB/MS analysis gives the following results $[M+H]^+=2920$.

The peptidic product of example 3 is represented by the following structure: AcEEED-β-A-β-A-RQIKIWFQNRRMKWKK-OH (SEQ ID No:2. Its formula is C131 H206 N40 O35 S1. Its molecular weight(M.W.) is 2933.4 Its FAB/MS analysis gives the following results [M+H]+2934.

The peptidic product of example 4 is represented by the following structure: AcEEED-RQIKIWFQNRRMKWKK-OH (SEQ ID No:3. Its formula is C125 H196 N38 O33 S1. Its molecular weight(M.W.) is 2791.3. Its FAB/MS analysis gives the following results $[M+H]^+2792$.

The peptidic product of example 5 is represented by the following structure: AcEEED-C-[S-S]-C-RQIKIWFQNRRMKWKK-OH (SEQ ID No:2. Its formula is C131 H206 N40 O36 S3. Its molecular weight(M.W.) is 2933.4. Its FAB/MS analysis gives the following results $[M+H]^+2934$.

The peptidic product of example 6 is represented by the following structure: α-(Biotinyl-GG), ε-(AcEEED)-K-RQIKIWFQNRRMKWKK-OH (SEQ ID No:4. Its formula is C145 H228 N44 O38 S2. Its molecular weight(M.W.) is 3259.8. Its FAB/MS analysis gives the following results $[M+H]^+3260$.

The peptidic product of example 7 is represented by the following structure: ε-(AcEEED)-K-RQIKIWFPNRRMKWKK-OH (SEQ ID No:1. Its formula is C131 H208 N40 O32 S1. Its molecular weight(M.W.) is 2887.4. Its ES/MS analysis gives the following results (M.W.) is 2887.6. ES/MS means Electrospray Mass Spectroscopy. General principle of ES/MS analysis is described in J. B. Fenn, M. Mann, C. K. Meng, C. M. Whitehouse, Science, 246, p. 64–71, 1989 or in R. D.

Smith, J. A. Loo, C. G. Edmonds, C. J. Barinaga, H. R. Udseth, Aral.chem., 62, p. 882–899, 1990.

The amino acid analysis of the peptide product of example 7 is as follows:

|       | Asp  | Glu  | Pro  | Met  | Ile  | Phe  | Trp | Lys  | Arg  |
|-------|------|------|------|------|------|------|-----|------|------|
| Theo. | 2    | 4    | 1    | 1    | 2    | 1    | 2   | 5    | 3    |
| Exp.  | 1.93 | 4.06 | 1.01 | 0.97 | 1.95 | 1.00 | —   | 4.95 | 3.12 |

Theo.=Theoretical, Exp.=Experimental eneral principle of amino acid analysis is described in S. Moore, W. H. Stein, J. Biol. Chem., 200, p. 803, 1953.

The peptidic product of example 8 is represented by the following structure: α-(BiotinylGG), ε-(AcEEED)-K-RQIKIWFPNRRMKWKK-OH (SEQ ID No:4). Its formula is C145 H228 N44 O36 S2. Its molecular weight(M.W.) is 3227.8. Its ES/MS analysis gives the following result 3227.2. The amino acid analysis of the peptide product of example 8 is as follows:

|       | Asp  | Glu  | Pro  | Gly  | Met  | Ile  | Phe  | Trp | Lys  | Arg  |
|-------|------|------|------|------|------|------|------|-----|------|------|
| Theo. | 2    | 4    | 1    | 2    | 1    | 2    | 1    | 2   | 5    | 3    |
| Exp.  | 1.89 | 4.10 | 1.02 | 2.02 | 0.98 | 1.95 | 1.01 | —   | 4.89 | 3.15 |

EXAMPLE 9

In Vitro Experiments
Concentration Dependence Assay

Peptidic products according to examples 1 to 8 show blocking effects on the binding anti-αSM-1 monoclonal antibody to the α-SM actin. A number of experiments were performed in order to investigate their efficiency to penetrate into the cells in culture and to interfere with α-SM actin organisation in stress fibers by the following tests.

After addition of the peptidic products to the culture medium, the cells have then been fixed, permeabilised and stained for α-SM actin and total actin (usual control for the penetration and effect of the peptide as described by Chaponnier et al. (1995)).

The peptidic products according to examples 1 to 8 were well active in inhibiting α-SM actin incorporation into stress fibers after inoculation on cultures of vascular smooth muscle cells (VSMC) for 3 hat different concentrations: 0.1, 0.2, 0.5, 1, 2 and 4 mg/ml (mg of peptidic product, ml of cell culture medium) in a medium comprising Dubelcco's Modified Eagle Medium (DMEM), Gibco Cat No 41965-039, Life Technologies, Basel, Switzerland, supplemented with 10% fetal calf serum and 20 mM Hepes (Gibco, Cat No 15630-056).

The VSMC were prepared by enzymatic digestion of rat aorta as described by Chaponnier et al. (1995) and Bochaton-Piallat et al. (Artherosclerosis and Vascular Biology Vol. 16, 815–820 (1996)).

Time Course Assay

A large number of experiments were performed with the peptidic products of examples 1 to 8 in order to assay more carefully the time course effect on the peptides. Said experiments were also used to investigate the location of the biotinylated peptides after delivery into the cells. The detection of the biotinylated peptides was assayed by staining with Fluorescein (FITC)-conjugated streptavidin (Jackson ImmunoResearch Laboratories, West Groves, Pa., USA), Cat No 016-090-084.

The peptidic products according to examples 1 to 8 were incubated in cultured VSMC at a concentration of 2 mg/ml for 3, 5, 10, 15, 30 and 60 minutes in a medium comprising Dubelcco's Modified Eagle Medium (DMEM), Gibco Cat No 41965-039, Life Technologies, Basel, Switzerland, supplemented with 10% fetal calf serum and 20 mM Hepes (Gibco, Cat No 15630-056).

Peptidic products of the examples 1 to 8 were able to inhibit the α-SM actin stress fiber organisation in 90% of the cells. The activity was clearly detectable already after 3 min of incubation. The localisation of the biotinylated peptides with stress fiber was difficult to obtain even in the early time. Most of the staining was localised at the membrane, with some diffuse staining in the cytoplasm. Strong staining was detected only in some cells during the first 15 min, and thereafter, staining appeared lighter in the cytoplasm but even in all cells. No FITC-streptavidin staining along the stress fibers was detectable even after longer time of peptides incubation.

Therefore, the incubation of the peptidic products of examples 1 to 8 into the cells appears to be particularly fast and may be difficult to follow by time course assay, but can be followed by using other marker peptides (i.e. fluorescent peptides), which allow "in live" observation of the peptides entry under the microscope.

Time course of α-SM actin recovery into stress fibers

The peptide products of examples 1 to 8 were incubated with cells for 3 hours in a medium comprising Dubelcco's Modified Eagle Medium (DMEM), Gibco Cat No 41965-039, Life Technologies, Basel, Switzerland, supplemented with 10% fetal calf serum and 20 mM Hepes (Gibco, Cat No 15630-056).

The cells were thereafter washed and the medium (medium without peptides) was left for different periods of time (15 min, 30 min, 1 h and 2 h).

These experiments show that α-SM positive stress fibers start to reorganise slightly after 1 hour, but clearly after 2 hours.

EXAMPLE 10

Incorporation Into the Cells using a Biotinylated Peptide

This experiment was used to control the entrance and exit ("in and out") of the peptidic product of example 6 (peptide α-(BiotynylGG),ε-(AcEEED)-K-(pAntp[43–58]) (SEQ ID No:4).

The VSMC cells were incubated in a medium comprising Dubelcco's Modified Eagle Medium (DMEM), Gibco Cat No 41965-039, Life Technologies, Basel, Switzerland, supplemented with 10% fetal calf serum and 20 mM Hepes (Gibco, Cat No 15630-056) 30 min with the peptidic product of example 6 and after withdrawal of the peptide, the cells were incubated with culture medium for 0, 5 min, 30 min, 1 h and 2 h. The cells were extracted after different times of incubation, in sample buffer comprising 0.08M Tris-Cl, ph 6.8; 2% sodium dodecyl sulfate (SDS); 0.1M Dithiothreitol (DTT); 0.001M phenylmethylsulfonyl fluoride (PMSF); 10% glycerol as described in Am. J. Pathol. 134:597–603, 1989, Gelsolin modulation in epithelial and stromal cells of mammary carcinoma, Chaponnier and Gabbiani.

The total protein extracts were run on a SDS-PAGE gel and transferred on a PVDF membrane, according to a method described in J. Cell Biol. 130:887–895, 1995, Chaponnier et al.

The membrane was then incubated with streptavidin peroxidase to detect the biotinylated peptide, according to a method described in Levy-Toledano et al. in Endocrinology 133:1803–1808,1993.

A strong signal was observed after 30 min peptide incubation and after 5 min withdrawal of the peptide, and a clear decrease after 30 min of washing and only a light signal after 1 hour withdrawal of the peptide. This experiment confirms the immunofluorescent staining as above-described and allows an assay to follow the possible "in and out" of the peptidic product into the cells.

EXAMPLE 11

Effect of the Peptidic Product on α-SM Actin Biosynthesis

Table 2 shows the results of four (4) experiments on the effect of the peptidic product of example 1 (peptidic product: α-(AcEEED)-K-(pAntp[43–58]) (SEQ ID No:1 on α-SM actin synthesis after 20 hours incubation time on VSMC in a medium comprising Dubeicco's Modified Eagle Medium (DMEM), Gibco Cat No 41965-039, Life Technologies, Basel, Switzerland, supplemented with 10% fetal calf serum and 20 mM Hepes (Gibco, Cat No 15630-056)at a temperature of 37° C.

TABLE 2

| Experiment | 1 | 2 | 3 | 4 | Mean |
|---|---|---|---|---|---|
| 0 hour | 100 | 100 | 100 | 100 | 100 |
| 20 hours | 72 | 56 | 44 | 48 | 55 |

In this table, the values of the control conditions were standardised at a 100% starting value (time=0 hour).

This table shows that the incubation of the peptidic product of example 1 (2 mg/ml culture medium) for hours provokes 55% decrease (mean value for the 4 experiments) of the α-SM actin synthesis (studied by means of $S^{35}$ methionine incorporation) compared to control conditions.

EXAMPLE 12

In Vivo Experiments

Test upon an open "splinted Wound" in Rats

In order to measure exclusively contraction, the inventors have developed the "splinted wound" model, based upon the technique of Gabbiani G. et al., J. of Exp.

Med. Vol. 135 pp. 719–734 (1972).

The wound 2×2 cm in the back of the rat is fixed by suturing its margins to a plastic frame using suture thread (Supramid, metric 3, Braun, Emmenbrücke) on day 0. This results in an inhibition of wound contraction while the development of granulation tissue is not affected. The peptidic product is applied on the open wound starting at the $7^{th}$ day usually for 3 days and releases the suture of the frame, thus allowing an accelerated contraction which in controls reduces the area of the wound of about ⅔ within 48 hours.

We have measured morphometrically the contraction of the wound (5 rats per group) by means of planimetry (KS 400, Zeiss Vision) and studied the tissues morphologically by means of histological techniques, immunofluorescence with the α-SM actin antibody according to a method described in Gabbiani et al., J. Exp. Med. 1972 (p.15, line 8) and Darby et al. Lab. Invest. 1990 (p.1, line 24–25).

Table 3 presents the wound size (surface in $cm^2$) measured on day 3 as a percentage of the wound size measured on day 0.

The rats were treated with the peptidic product of example 1 at a dose of 3 mg/ml (mg of peptidic product, ml of 0.9% NaCl).

TABLE 3

| Treatment | Wound surface* |
|---|---|
| (0.9% NaCl) saline solution | 30.59 ± 1.57 |
| Peptidic product of example 1 | 48.42 ± 2.02 |

This result suggests a decrease in contractile activity when the rats were treated topically with the peptidic product of example 1 at dose of 3 mg/ml.

What is claimed is:

1. A peptidic product comprising the tetrapeptide Acetyl-glutamyl-glutamyl-glutamyl-aspartyl (SEQ ID No: 5) associated with a chemical entity that is able to introduce said tetrapeptide into a cell, wherein the chemical entity is a polypeptide of at least 8 amino acids.

2. The peptidic product according to claim 1, wherein the polypeptide is the tat mediated protein.

3. The peptidic product according to claim 1, wherein the polypeptide is a homeobox polypeptide.

4. The peptidic product according to claim 1, wherein the tetrapeptide is linked to the chemical entity through a spacer.

5. The peptidic product according to claim 1, which is selected from the group consisting of ε-(AcEEED)-K-RQIKIWFQNRRMKWKK-OH (SEQ ID No: 1), AcEEED-K-RQIKIWFQNRRMKWKK-OH (SEQ ID No: 1), AcEEED-β-A-β-A-RQIKIWFQNRRMKWKK-OH (SEQ ID No: 2), AcEEED-RQIKIWFQNRRMKWKK-OH (SEQ ID No: 3); AcEEED-C-(S-S)-C-RQIKIWFQNRRMKWKK-OH (SEQ ID No: 2); α-(BiotynylGG), ε-(AcEEED)-K-RQIKIWFQNRRMKWKK-OH (SEQ ID No: 4); ε-(AcEEED)-K-RQIKIWFPNRRMKWKK-OH (SEQ ID No: 1) and α-(BiotynylGG), α-(AcEEED)-K-RQIKIWFPNRRMKWKK-OH (SEQ ID No: 4).

6. A pharmaceutical composition comprising at least one pharmaceutically acceptable excipient and an effective amount of the peptidic product according to claim 1.

7. A method of making a pharmaceutical composition which comprises mixing an effective amount of the peptidic product according to claim 1 with at least one pharmaceutically acceptable excipient.

8. A method for prevention or treatment of a disease related to α-SM actin expression and contractile activity in a cell, which comprises administering to a patient in need thereof a therapeutically effective amount of the peptidic product according to claim 1.

9. The method according to claim 8, wherein the disease is selected from the group consisting of wound contraction, hypertrophic scars, fibromatosis and fibrotic conditions.

10. The method according to claim 8, wherein the disease is selected from the group consisting of Dupuytren's disease and pulmonary fibrosis.

11. A method of interfering with α-SM actin organization in stress fibers or of inhibiting α-SM actin incorporation into stress fibers and thereby inhibiting myofibroblast contraction, said method comprising administering an effective amount of the peptidic product according to claim 1.

12. The method according to claim 11, wherein the disease is selected from the group consisting of wound contraction, hypertrophic scars, fibromatoses and fibrotic conditions.

13. The method according to claim 11, wherein the disease is selected from the group consisting of Dupuytren's disease and pulmonary fibrosis.

* * * * *

SEQUENCE LISTING

<160> NUMBER OF SEQ ID NOS:  7

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: Residue
<222> LOCATION: (13)
<223> OTHER INFORMATION: Gln or Pro

<400> SEQUENCE: 1

Glu Glu Glu Asp Lys Arg Gln Ile Lys Ile Trp Phe Xaa Asn Arg Arg
 1               5                  10                  15

Met Lys Trp Lys Lys

20

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: Residue
<222> LOCATION: (5)
<223> OTHER INFORMATION: Cys or beta-Ala
<221> NAME/KEY: Residue
<222> LOCATION: (6)
<223> OTHER INFORMATION: Cys, if Residue 5 is Cys, or beta-Ala, if
      Residue 5 is beta-Ala.
<221> NAME/KEY: Residue
<222> LOCATION: (14)
<223> OTHER INFORMATION: Gln or Pro

<400> SEQUENCE: 2

Glu Glu Glu Asp Xaa Xaa Arg Gln Ile Lys Ile Trp Phe Xaa Asn Arg
 1               5                  10                  15

Arg Met Lys Trp Lys Lys
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: Residue
<222> LOCATION: (12)
<223> OTHER INFORMATION: Gln or Pro

<400> SEQUENCE: 3

Glu Glu Glu Asp Arg Gln Ile Lys Ile Trp Phe Xaa Asn Arg Arg Met
 1               5                  10                  15

Lys Trp Lys Lys
            20

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: Residue
<222> LOCATION: (15)
<223> OTHER INFORMATION: Gln or Pro

<400> SEQUENCE: 4

Gly Gly Glu Glu Glu Asp Lys Arg Gln Ile Lys Ile Trp Phe Xaa Asn
 1               5                  10                  15

Arg Arg Met Lys Trp Lys Lys
            20

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

```
Glu Glu Glu Asp
 1

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Glu Glu Glu Asp Ser Thr Ala Leu Val Cys
 1               5                  10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: Residue
<222> LOCATION: (8)
<223> OTHER INFORMATION: Gln or Pro

<400> SEQUENCE: 7

Arg Gln Ile Lys Ile Trp Phe Xaa Asn Arg Arg Met Lys Trp Lys Lys
 1               5                  10                  15
```